(12) United States Patent
Mori et al.

(10) Patent No.: US 10,835,762 B2
(45) Date of Patent: Nov. 17, 2020

(54) MEDICAL APPARATUS AND METHOD

(71) Applicant: Toshiba Energy Systems & Solutions Corporation, Kawasaki (JP)

(72) Inventors: Shinichiro Mori, Chiba (JP); Koki Yanagawa, Tokorozawa (JP); Ryusuke Hirai, Shinagawa (JP); Shinya Fukushima, Fuchu (JP); Yasushi Iseki, Yokohama (JP); Keiko Okaya, Setagaya (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 168 days.

(21) Appl. No.: 16/223,492

(22) Filed: Dec. 18, 2018

(65) Prior Publication Data

US 2019/0184199 A1    Jun. 20, 2019

(30) Foreign Application Priority Data

Dec. 20, 2017  (JP) .................................. 2017-244072

(51) Int. Cl.
*A61N 5/10* (2006.01)
(52) U.S. Cl.
CPC ......... *A61N 5/1049* (2013.01); *A61N 5/1037* (2013.01); *A61N 5/1067* (2013.01);
(Continued)
(58) Field of Classification Search
None
See application file for complete search history.

(56) References Cited

U.S. PATENT DOCUMENTS 10,327,717 B2 * 6/2019 Melman ................... A61B 6/54
2005/0053196 A1 3/2005 Mostafavi
(Continued)

FOREIGN PATENT DOCUMENTS

EP    3 466 488 A1    4/2019
JP    2016-106756 A   6/2016
(Continued)

*Primary Examiner* — Hoon K Song
(74) *Attorney, Agent, or Firm* — Oblon, McClelland, Maier & Neustadt, L.L.P.

(57) ABSTRACT

A medical apparatus according to an embodiment includes an acquirer, an identifier, and a controller. The acquirer acquires a fluoroscopic image of an object from an imager which performs imaging by irradiating the object with an electromagnetic wave to generate the fluoroscopic image. The identifier identifies a target position of the object in the fluoroscopic image. The controller outputs an irradiation permission signal to a therapeutic device which irradiates the object with a therapeutic beam in a case where the target position identified by the identifier is settled within an irradiation permission range. The controller is configured to cause the imager to stop performing irradiation of the electromagnetic wave and cause the acquirer to stop acquiring the fluoroscopic image, in a case where a first switch is operated, and the controller is configured to cause the imager to stop performing irradiation of the electromagnetic wave and maintain a state in which the acquirer is capable of acquiring the fluoroscopic image, in a case where a second switch is operated.

14 Claims, 7 Drawing Sheets

(52) U.S. Cl.
CPC ............... *A61N 2005/1061* (2013.01); *A61N 2005/1074* (2013.01)

(56) References Cited

U.S. PATENT DOCUMENTS

| | | |
|---|---|---|
| 2014/0343401 A1 | 11/2014 | Huber et al. |
| 2015/0087881 A1* | 3/2015 | Miyamoto ............ A61B 6/5211 600/1 |
| 2016/0082284 A1 | 3/2016 | Ooga et al. |
| 2017/0231586 A1 | 8/2017 | Hirai et al. |
| 2018/0193670 A1* | 7/2018 | Taguchi ............... A61N 5/1049 |
| 2019/0070437 A1* | 3/2019 | Olcott ................. A61N 5/1049 |
| 2019/0143148 A1 | 5/2019 | Fujii et al. |

FOREIGN PATENT DOCUMENTS

| | | |
|---|---|---|
| JP | 2017-144000 | 8/2017 |
| WO | WO 2017/203998 A1 | 11/2017 |

\* cited by examiner

MEDICAL APPARATUS AND METHOD

CROSS-REFERENCE TO RELATED APPLICATION

This application is based upon and claims the benefit of priority from Japanese Patent Application No. 2017-244072 filed on Dec. 20, 2017; the entire content of which is incorporated herein by reference.

BACKGROUND OF THE INVENTION

Field of the Invention

Embodiments described herein relate generally to a medical apparatus and method.

Description of Related Art

Therapeutic devices which irradiate a patient (object) with a therapeutic beam such as a heavy particle beam or a radiation are known. There are cases in which a lesion of an object, that is, a spot to be irradiated with a therapeutic beam moves due to respirations, heartbeat, intestinal movements, and the like. As a therapeutic method suitable therefor, a gated irradiation method and a tracking irradiation method are known.

In a case where a lesion which moves due to respirations is irradiated with a therapeutic beam, there is a need to perform irradiation synchronously with respiratory phases of an object. Techniques of respiratory phase synchronization include a technique of ascertaining the respiratory phase (external respiratory synchronization) by utilizing output values of various sensors attached to the body of an object, and a technique of ascertaining the respiratory phase (internal respiratory synchronization) based on a fluoroscopic image of an object. The processing for respiratory phase synchronization is performed by a medical apparatus which outputs a control signal to a therapeutic device. For example, a medical apparatus controls a therapeutic device by performing wired or wireless communication with the therapeutic device.

For example, a therapy of this kind can be performed while a fluoroscopic image of the inside of the body of a patient is captured by using an X-ray or the like. For example, such imaging can be stopped in a case where the condition of a patient has been improved, or in a case where a physician or the like temporarily stops his/her hand movement, in addition to a case in which a therapy has ended, and a case in which abnormality has occurred such that a therapy cannot be restarted. However, in technologies in the related art, it sometimes takes time to restart imaging after such cases of stopping imaging, and there are cases in which efficiency deteriorates.

SUMMARY OF THE INVENTION

An object to be achieved by the present invention is to provide a medical apparatus and method, which is capable of improving efficiency of a therapy.

A medical apparatus according to an embodiment includes an acquirer, an identifier, and a controller. The acquirer acquires a fluoroscopic image of an object from an imager which performs imaging by irradiating the object with an electromagnetic wave to generate the fluoroscopic image. The identifier identifies a target position of the object in the fluoroscopic image. The controller outputs an irradiation permission signal to a therapeutic device which irradiates the object with a therapeutic beam in a case where the target position identified by the identifier is settled within an irradiation permission range. The controller is configured to cause the imager to stop performing irradiation of the electromagnetic wave and cause the acquirer to stop acquiring the fluoroscopic image, in a case where a first switch is operated, and the controller is configured to cause the imager to stop performing irradiation of the electromagnetic wave and maintain a state in which the acquirer is capable of acquiring the fluoroscopic image, in a case where a second switch is operated.

According to the present embodiment, it is possible to provide a medical apparatus and method, which is capable of improving efficiency of a therapy.

DETAILED DESCRIPTION OF THE INVENTION

Hereinafter, a medical apparatus and method according to an embodiment will be described with reference to the drawings. In this application, the expression "based on XX" denotes "based on at least XX" and also includes a case based on another element in addition to XX. The expression "based on XX" is not limited to a case of directly adopting XX and also includes a case based on a result realized by performing computation or processing with respect to XX. The term "XX" indicates an arbitrary element (for example, arbitrary information).

Configuration

Figure 1:
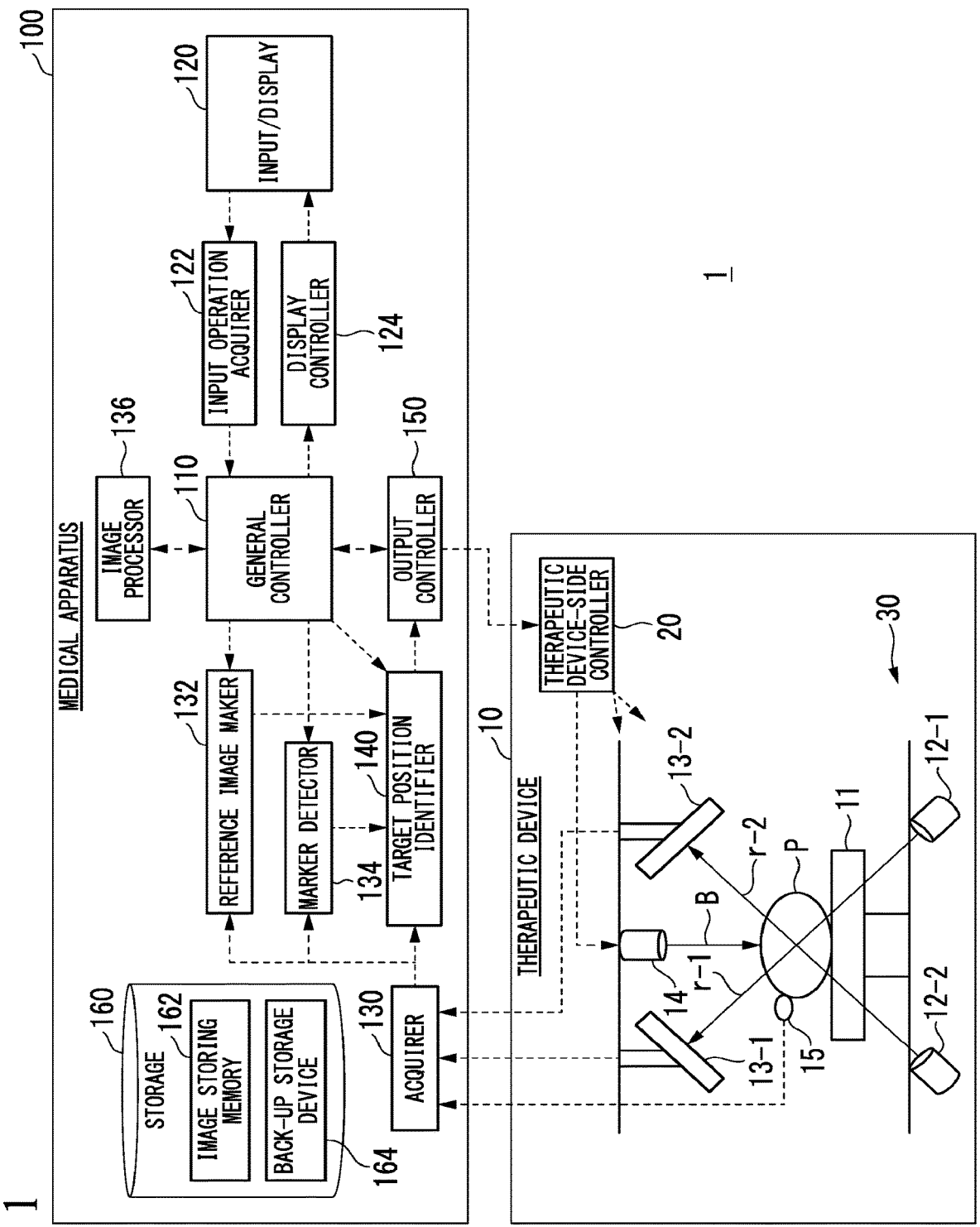
FIG. 1 is a configuration diagram of a therapy system 1 including a medical apparatus 100.

FIG. 1 is a configuration diagram of a therapy system 1 including a medical apparatus 100. For example, the therapy system 1 includes a therapeutic device 10 and the medical apparatus 100.

For example, the therapeutic device 10 includes a bed 11, radiation sources 12-1 and 12-2, detectors 13-1 and 13-2, an irradiation gate 14, a sensor 15, and a therapeutic device-side controller 20. Hereinafter, a hyphen and a numeral following it in the reference sign indicate a fluoroscopic radiation or a fluoroscopic image realized by a set of a radiation source and a detector. Suitably, the hyphen and the numeral following it in the reference sign may be omitted in description.

An object P to be treated is fixed to the bed 11. The radiation source 12-1 irradiates the object P with a radiation r-1. The radiation source 12-2 irradiates the object P with a radiation r-2 at an angle different from that of the radiation source 12-1. The radiations r-1 and r-2 are examples of electromagnetic waves and are X-rays, for example. Hereinafter, description will be given on this premise.

The radiation r-1 is detected by the detector 13-1, and the radiation r-2 is detected by the detector 13-2. For example, the detectors 13-1 and 13-2 are flat panel detectors (FPD), image intensifiers, or color image intensifiers. The detector 13-1 detects energy of the radiation r-1, performs digital conversion, and outputs the conversion result to the medical apparatus 100 as a fluoroscopic image TI-1. The detector 13-2 detects energy of the radiation r-2, performs digital conversion, and outputs the conversion result to the medical apparatus 100 as a fluoroscopic image TI-2. In FIG. 1, two sets of the radiation source and the detector are illustrated. However, the therapeutic device 10 may include three or more sets of the radiation source and the detector.

In a therapy stage, the irradiation gate 14 irradiates the object P with a therapeutic beam B. Examples of the therapeutic beam B include a heavy particle beam, an X-ray, a γ-ray, an electron beam, a proton beam, and a neutron beam. In FIG. 1, only one irradiation gate 14 is illustrated. However, the therapeutic device 10 may include a plurality of irradiation gates. Hereinafter, the radiation sources 12-1 and 12-2 and the detectors 13-1 and 13-2 will be generically referred to as an imager 30.

The sensor 15 is provided to recognize an external respiratory phase of the object P and is attached to the body of the object P. For example, the sensor 15 is a pressure sensor.

The therapeutic device-side controller 20 operates the radiation sources 12-1 and 12-2, the detectors 13-1 and 13-2, and the irradiation gate 14 in response to a control signal from the medical apparatus 100.

For example, the medical apparatus 100 includes a general controller 110, an input/display 120, an input operation acquirer 122, a display controller 124, an acquirer 130, a reference image maker 132, an image processor 136, a target position identifier 140, an output controller 150, and a storage 160. For example, at least a part of each of the general controller 110, the input operation acquirer 122, the display controller 124, the acquirer 130, the reference image maker 132, the image processor 136, the target position identifier 140, and the output controller 150 is realized by a hardware processor such as a central processing unit (CPU) or a graphics processing unit (GPU) executing a program (software) stored in the storage 160. A part or all of these constituent elements may be realized by hardware (circuit section; including circuitry) such as a large scale integration (LSI), an application specific integrated circuit (ASIC), a field-programmable gate array (FPGA), or a graphics processing unit (GPU) or may be realized by cooperation of software and hardware.

Hereinafter, the function of each part of the medical apparatus 100 will be described. In description of the medical apparatus 100, unless otherwise identified, processing performed with respect to the fluoroscopic image TI will be regarded to be executed with respect to both the fluoroscopic images TI-1 and TI-2. The general controller 110 generally controls the functions of the medical apparatus 100.

The input/display 120 is an example of "a display". For example, the input/display 120 includes a display device such as a liquid crystal display (LCD), an organic electroluminescence (EL) display device, or a light emitting diode (LED) display; and an input device which receives an input operation performed by an operator. The input/display 120 may be a touch panel in which a display device and an input device are integrally formed or may include an input device such as a mouse and a keyboard.

The input operation acquirer 122 recognizes the details of an operation (touching, flicking, swiping, clicking, dragging, key-inputting, or the like) performed with respect to the input/display 120 and outputs the details of the recognized operation to the general controller 110. The display controller 124 causes the input/display 120 to display an image in response to an instruction from the general controller 110. The display controller 124 causes the input/display 120 to display an interface screen for receiving an instruction to start each of a preparation stage of a therapy and an irradiation stage of the therapeutic beam B. Displaying of an image includes generation of elements of an image performed based on a computation result and allocation of elements of an image made in advance to a display screen.

The acquirer 130 acquires the fluoroscopic image TI from the therapeutic device 10. The acquirer 130 acquires a detection value of the sensor 15. The acquirer 130 acquires three-dimensional volume data of the object P from a medical inspection device (not illustrated). In a case where the fluoroscopic image TI is used as a reference image to identify the position of a target, the reference image maker 132 generates a reference image to be used for identifying a target position, based on the fluoroscopic image TI acquired by the acquirer 130. These will be described below in detail.

The image processor 136 performs image processing such as deformable registration and a digitally reconstructed radiograph (DRR) image generation. Deformable registration is processing performed with respect to time-series three-dimensional volume data, in which positional information designated for three-dimensional volume data at a certain point of time is deployed in three-dimensional volume data at another point of time. A DRR image is a virtual fluoroscopic image generated by irradiating three-dimensional volume data with a radiation from a virtual radiation source.

The target position identifier 140 is an example of "an identifier". The target position identifier 140 identifies the position of a target in the fluoroscopic image TI. A target position may be a lesion of the object P, that is, a position to be irradiated with the therapeutic beam B, or may be a marker or a characteristic spot of the object P. Since the difference between a characteristic spot such as the diaphragm, the heart, or a bone and surrounding spots appears in a relatively clear manner in the fluoroscopic image TI, the characteristic spot is a spot of which the position can be easily identified in a case where a computer analyzes the fluoroscopic image TI. The target position may be one point or a region having a two-dimensional or three-dimensional spread.

The output controller 150 outputs an irradiation permission signal to the therapeutic device 10 based on the target position identified by the target position identifier 140. For example, in a gated irradiation method, in a case where the target position is settled within a gating window, the output controller 150 outputs a gate-on signal to the therapeutic device 10. A gating window is a region set in a two-dimensional plane or a three-dimensional space and is an example of an irradiation permission range. A gate-on signal is a signal for instructing an operator to irradiate the object P with the therapeutic beam B and is an example of an irradiation permission signal. Hereinafter, description will be given on these premises. The therapeutic device 10 performs irradiation of the therapeutic beam B in a case where a gate-on signal is input, and does not perform irradiation of the therapeutic beam B in a case where no gate-on signal is input. The irradiation permission range is not limited to a fixedly set range and may be a range which moves in a manner following a movement of a lesion. The general controller 110 and the output controller 150 are examples of "a controller".

For example, the storage 160 is realized by a random access memory (RAM), a read only memory (ROM), a hard disk drive (HDD), or a flash memory. The storage 160 stores time-series three-dimensional CT images (hereinafter, 4D CT images), the fluoroscopic image TI, an output value of the sensor 15, and the like, in addition to the program described above. For example, the storage 160 includes an image storing memory 162 and a back-up storage device 164. The image storing memory 162 is an example of "a memory". The hack-up storage device 164 is an example of "a storage device". The image storing memory 162 and the back-up storage device 164 are realized by a RAM or a ROM, an HDD, and a flash memory, for example.

For example, the image storing memory 162 temporarily stores the captured fluoroscopic image TI. For example, after a therapy ends, the back-up storage device 164 stores the fluoroscopic image TI, as back-up data, which is temporarily stored in the image storing memory 162. As described above, the program described above, 4D CT images, and the like are also stored in the storage 160.

Flow of Therapy

Hereinafter, a flow of a therapy in the therapy system 1 will be described. Hereinafter, description will be given on the premise that a therapy is performed based on markerless tracking which is internal respiratory synchronization using no marker. However, a therapy may he performed based on marker tracking which is internal respiratory synchronization using a marker, or external respiratory synchronization. Markerless tracking includes a technique of using a template matching method or machine learning. Hereinafter, markerless tracking using the template matching method will be described, and description will be given such that the gated irradiation method is employed as an irradiation method. The medical apparatus 100 may be switchable between the template matching method and a technique using machine learning.

Figure 2:
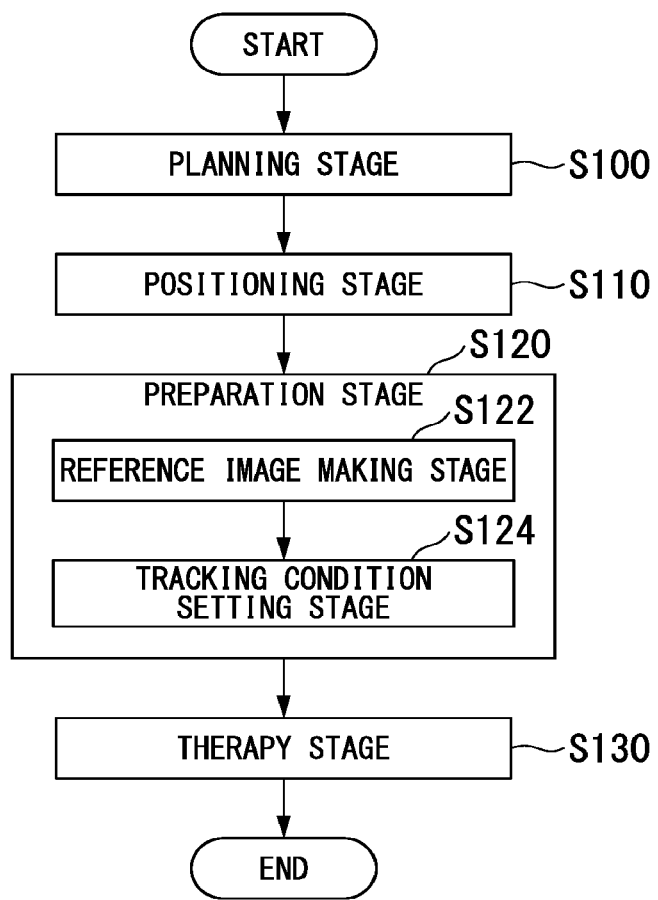
FIG. 2 is a flowchart illustrating an example of a flow of a therapy in the therapy system 1.

FIG. 2 is a flowchart illustrating an example of a flow of a therapy in the therapy system 1. A therapy is broadly divided into a planning stage (Step S100), a positioning stage (Step S110), the preparation stage (Step S120), and the therapy stage (Step S130). The preparation stage is further divided into a reference image making stage (Step S122) and a tracking condition setting stage (Step S124). Hereinafter, an overview of each stage will be described.

Planning Stage

In the planning stage (Step S100), first, CT imaging of the object P is performed. In CT imaging, images of the object P are captured in various directions for each of various respiratory phases. Next, 4D CT images are generated based on the results of the CT imaging. 4D CT images are n three-dimensional CT images (an example of the three-dimensional volume data described above) arranged in time series. A period obtained by multiplying this number n by the time interval between the time-series images is set to cover a period in which the respiratory phase changes by one cycle, for example 4D CT images are stored in the storage 160.

Next, a physician, a radiologist, or the like inputs a contour with respect to one CT image of n CT images, for example. This contour is a contour of a tumor which is a lesion or a contour of an organ which is not intended to be irradiated with the therapeutic beam B. Next, for example, the image processor 136 sets the contour for each of n CT images through deformable registration. Next, a therapeutic plan is decided. A therapeutic plan is a plan for regulating irradiation of the place, the direction, and the quantity of the therapeutic beam B in accordance with the position of a lesion based on information of the set contour. The therapeutic plan is decided in accordance with a therapeutic method such as the gated irradiation method or a tracking irradiation method. A part or all of the processing in the planning stage may be executed by an external device. For example, processing of generating 4D CT images may be executed by a CT device.

Here, a region defined by the contour of a tumor, the center of gravity in this region, the position of a characteristic spot of the object P, or the like becomes a target position. Moreover, in the therapeutic plan, the position which may be irradiated with the therapeutic beam B is decided as a target position. In a case where the contour is set through deformable registration, a margin is automatically or manually set for the target position, and a gating window is set by applying the margin. This margin is provided to absorb an error in the device, positioning, and the like.

Positioning Stage

In the positioning stage (Step S110), the bed position is adjusted. The object P is laid on the bed 11 and is fixed by using a shell or the like. First, the bed position is roughly adjusted.

In this stage, a worker visually checks for the position and the posture of the object P and moves the bed 11 to a position at which the object P will be irradiated with the therapeutic beam B from the irradiation gate 14. Accordingly, the position of the bed 11 is roughly adjusted. Next, an image to be utilized for minutely adjusting the bed position is captured. For example, in a case where 3D-2D registration is performed, the fluoroscopic image TI is captured. For example, the fluoroscopic image TI is captured at the timing of the end of exhalation of the object P. Since the position of the bed 11 has already been roughly adjusted, an area near a lesion of the object P is imaged in the fluoroscopic image TI.

In a case where 3D-2D registration is performed, in this stage, a DRR image is generated from three-dimensional volume data by using the radiation sources 12-1 and 12-2, the detectors 13-1 and 13-2, and the therapeutic plan information of the object P. The movement amount of the bed is calculated based on the DRR image and the fluoroscopic image TI, and the bed 11 is moved. The position of the bed 11 is minutely adjusted by repeating capturing the fluoroscopic image TI, calculating the movement amount of the bed, and moving the bed 11.

Preparation Stage (Part 1: Reference Image Making Stage)

In a case where the positioning stage ends, the processing shifts to the preparation stage (Step S120). In the reference image making stage (Step S122) of the preparation stage, a reference image is made. First, a DRR image of each phase is made from 4D CT images. The DRR image may be made at any time after the 4D CT images have been captured. In this case, a position, at which the gating window set in the therapeutic plan is projected, is set as the gating window on the DRR image. In the preparation stage, first, the fluoroscopic image TI is captured to make a reference image. For example, in the reference image making stage, after imaging is started, imaging is performed for only a predetermined period. For example, imaging is performed for a period of a respiratory cycle designated in advance. For example, the fluoroscopic images TI for k times of respirations, which are necessary and sufficient to learn the relationship between a reference image and a target position PT, are captured. For example, the fluoroscopic image TI is captured such that two respirations of the object P are covered. While the object P performs deep respirations, an external respiratory waveform of the object P is acquired synchronously with the fluoroscopic image TI. The display controller 124 causes the input/display 120 to display the acquired external respiratory waveform. A tracking value on the fluoroscopic image TI derived out by the image processor 136 based on the target position of a DRR image is associated with the captured fluoroscopic image TI. The tracking value may be obtained from the external respiratory waveform.

In this stage, the relationship between the fluoroscopic image TI and the target position is learned from information of the DRR image and the target position on the DRR image. Moreover, correction of the target position by a physician is received. From the fluoroscopic image TI in which the target position has been learned, one or more templates (reference images) are selected based on the tracking value. A template may be a cut-out characteristic part of this fluoroscopic image TI. Learning of the target position may be performed at any timing during a period from the planning stage to the therapy stage.

Preparation Stage (Part 2: Tracking Condition Setting Stage)

Subsequently, in the tracking condition setting stage (Step S124) of the preparation stage, tracking of a target position is checked for and the output timing of a gate-on signal is checked for. First, capturing the fluoroscopic image TI is started. The target position identifier 140 performs matching of the template with respect to the fluoroscopic images TI input in time series and allocates the target position with respect to the fluoroscopic image TI. While causing the input/display 120 to display the fluoroscopic images TI as a moving image, the display controller 124 causes the target position to be displayed in a manner of being superimposed on a frame of the fluoroscopic image TI in which the target position is allocated. As a result, the tracking results of the target position are checked by a physician or the like.

In this case, the display controller 124 causes the gating window set on the DRR image to be displayed on the fluoroscopic image TI. The output controller 150 determines whether or not the target position is settled within the gating window, regarding both the fluoroscopic images TI-1 and TI-2. In the therapy stage, a gate-on signal is output to the therapeutic device 10 in a case where the target position is settled within the gating window. However, in the preparation stage, the presence or absence of an output of a gate-on signal is transmitted to the display controller 124 via the general controller 110. The display controller 124 causes the input/display 120 to display the presence or absence of an output of a gate-on signal in parallel with displaying of the moving image. As a result, the output timing of a gate-on signal is checked by a physician or the like.

Therapy Stage

In the therapy stage (Step S130), the output controller 150 outputs a gate-on signal to the therapeutic device 10 in a case where the target position is settled within the gating window, regarding both the fluoroscopic images TI-1 and TI-2. Accordingly, a therapy is performed by irradiating a lesion of the object P with the therapeutic beam B. In the case in which the target position is the position of a lesion, irradiation of the therapeutic beam B is performed in a case where the tracked target position is settled within the gating window. In the case in which the target position is the position of a characteristic spot of the object P, irradiation of the therapeutic beam B is performed in a case where the position of a lesion derived out from the target position is settled within the gating window, based on the relationship between the target position learned in advance and the position of a lesion. A portion at the position of a lesion may be irradiated with the therapeutic beam B by these complex techniques. That is, irradiation of the therapeutic beam B may be performed in a case where a lesion is settled within a first gating window and a characteristic spot is settled within a second gating window, by setting each of the position of a lesion and the position of a characteristic spot as the target position.

Display Image and Flowchart

Processing of the medical apparatus 100 for supporting the flow of a therapy described above will be described.

Figure 3:
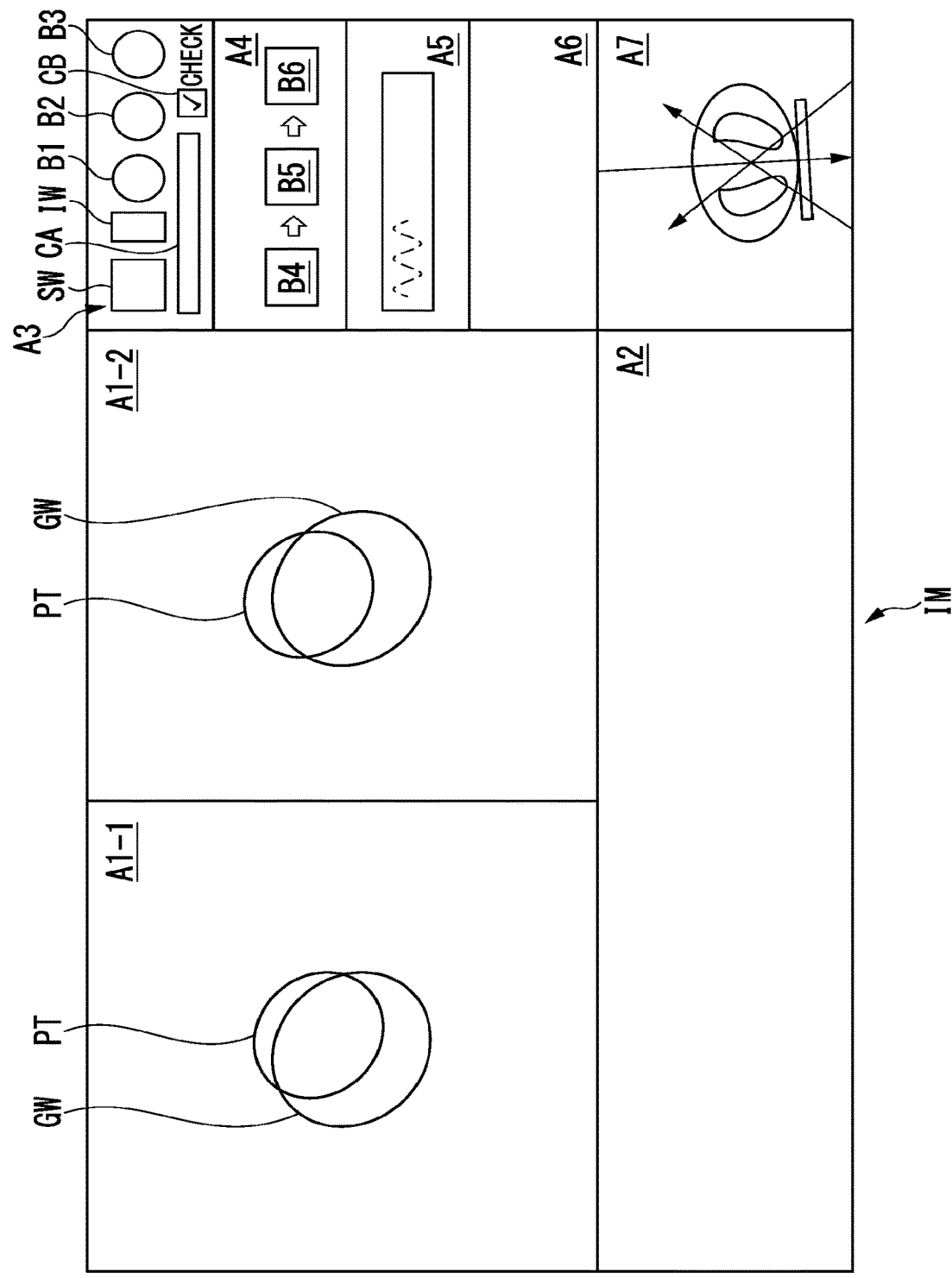
FIG. 3 is a view illustrating an example of an interface image IM displayed by an input/display 120 of the medical apparatus 100.

FIG. 3 is a view illustrating an example of an interface image IM which is displayed by the input/display 120 of the medical apparatus 100. For example, the interface image IM includes regions A1-1, A1-2, A2, A3, A4, A5, A6, and A7.

In the region A1-1, a gating window GW or the target position PT is displayed in a manner of being superimposed on the fluoroscopic image TI-1. In the region A1-2, the gating window GW or the target position PT is displayed in a manner of being superimposed on the fluoroscopic image TI-2. In the region A2, various graphs and the like are displayed.

In the region A3, a selection window SW for receiving selection of a mode and the like, an icon window IW for showing the presence or absence of an output of a gate-on signal, a first button B1 for instructing the therapeutic device 10 to start capturing or stop capturing the fluoroscopic image TI, a second button B2 for instructing the therapeutic device 10 to temporarily stop capturing or restart capturing the fluoroscopic image TI, a third button B3 for instructing the therapeutic device 10 to end a therapeutic session, a slide bar for tracing back and checking for DRR images or the fluoroscopic images TI in time series, a control area CA in which a frame advancing switch and the like are set, a check box CB for checking for completion of the preparation stage, and the like are set. For example, an operation with respect to each part of the interface image IM is performed by performing a touching operation, clicking a mouse, operating a keyboard, or the like. For example, the first button B1 is operated by performing a touching operation or clicking a mouse.

Figure 4:
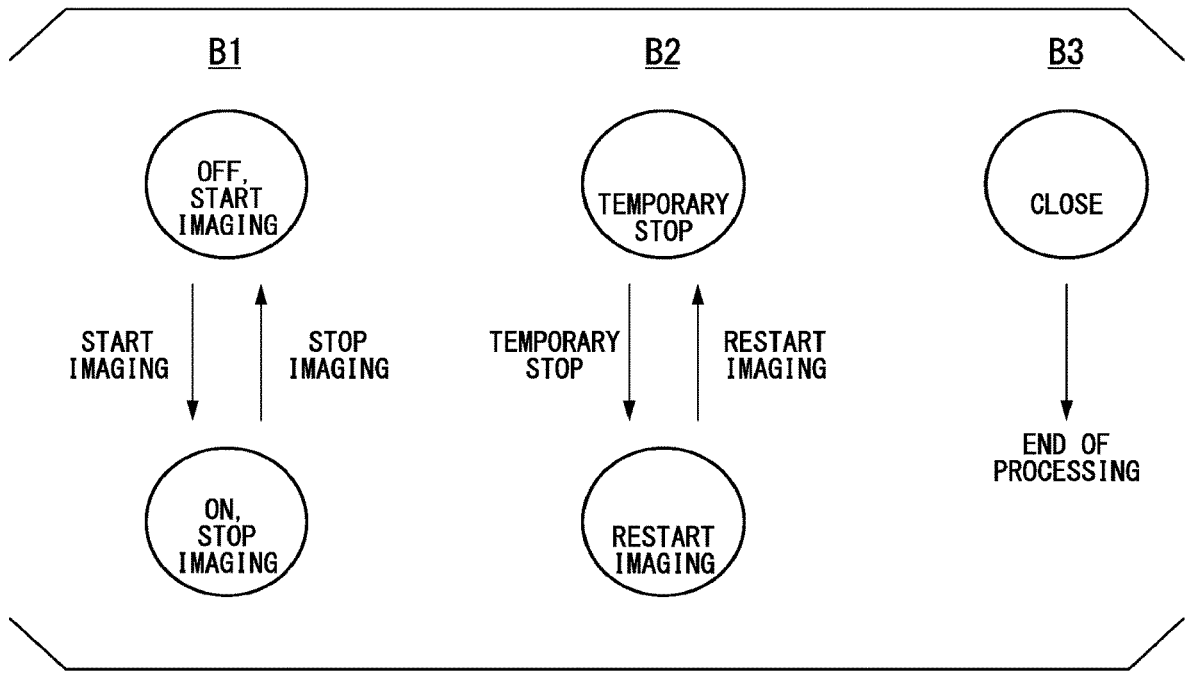
FIG. 4 is a view illustrating a change in a form of displaying a first button B1, a second button B2, and a third button B3.

FIG. 4 is a view illustrating a change in a form of displaying the first button B1, the second button B2, and the third button B3. For example, as illustrated in the diagram, in an initial state, the first button B1 indicates a state in which imaging is "OFF", that is, stopped in a first form of receiving an instruction for "start imaging". In a case where the first button B1 is operated, a state in which imaging is "ON", that is, executed is indicated, and the first button B1 changes into a second form of receiving an instruction for "stop imaging". The first button B1 performs state transition between these two forms. For example, the general controller 110 instructs the display controller 124 to cause the input/display 120 to display an image of the first button B1 including "OFF" and the characters of "start imaging" in an initial state. For example, in a case where the first button B1 is operated, the general controller 110 instructs the display controller 124 to cause the input/display 120 to display an image of the first button B1 including "ON" and the characters of "stop imaging".

Figure 5:
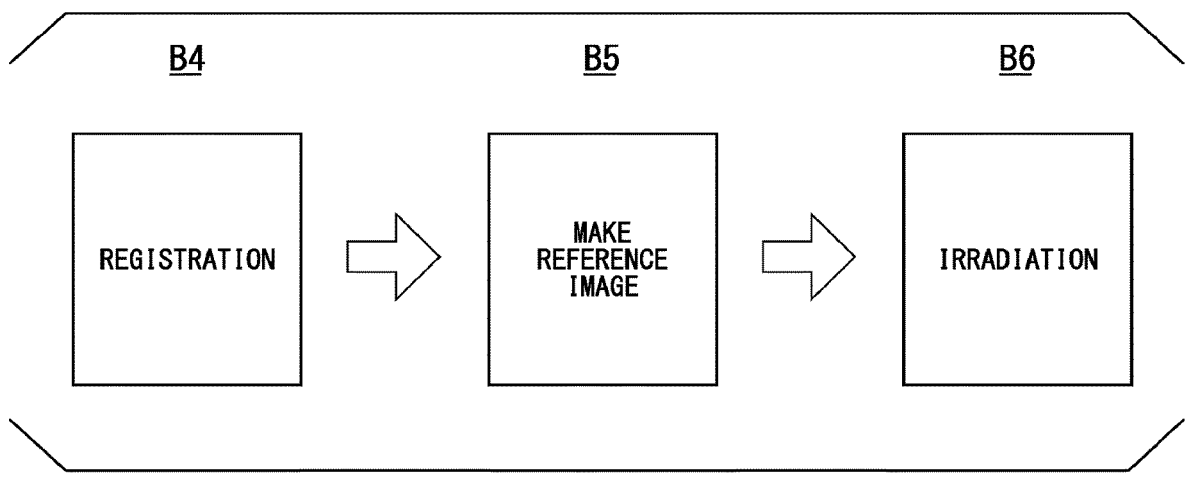
FIG. 5 is a view illustrating details of a fourth button B4, a fifth button B5, and a sixth button B6.

In an initial state, the second button B2 is in a third form of receiving an instruction for "temporary stop" of imaging in a case where being operated. In a case where being operated, the second button B2 changes into a fourth form of receiving an instruction for "restart imaging". For example, in an initial state, the general controller 110 instructs the display controller 124 to cause the input/display 120 to display an image of the second button B2 including the characters of "temporary stop". For example, in a case where the second button B2 is operated, the general controller 110 instructs the display controller 124 to cause the input/display 120 to display an image of the second button B2 including the characters of "restart imaging". In an initial state, the third button B3 is in a form of receiving an instruction for "close" of the interface image IM. In a case where the third button B3 is operated, the interface image IM is stopped being displayed, and a series of processing ends. Here, the second form of the first button B1 for receiving an instruction for "stop imaging" is an example of "a first switch". The third form of the second button B2 for receiving an instruction for "temporary stop" is an example of "a second switch". The first form of the first button B1 for receiving an instruction for "start imaging" is an example of "a third switch". The details of the first button B1 and the second button B2 will be described below in detail. Hereinafter, description of changes in displaying of the first button 131 and the second button B2 in the input/display 120 in a case where the first button B1 and the second button B2 are operated will be omitted. In the region A4, a fourth button B4, a fifth button B5, and a sixth button B6 for instructing the therapeutic device 10 that the therapy stage corresponding to the mode proceeds to a next step are set. FIG. 5 is a view illustrating details of the fourth button B4, the fifth button B5, and the sixth button B6. The fourth button B4 receives an instruction for registration (learning of the target position PT in the fluoroscopic image TI), the fifth button B5 receives an instruction for making a reference image, and the sixth button B6 receives an instruction for checking for a gate-on signal.

In the region A5, the graph of the external respiratory waveform based on the output value of the sensor 15, and the like are displayed.

In the region A6, an image indicating the therapeutic plan information of the object P, and text information are displayed. In the region A7, the irradiation direction of an X-ray, the irradiation field, the irradiation direction of the therapeutic beam B, the contour of a target, the marker ROI, and the like are displayed in a manner of being superimposed on a cross section of a CT image of the object P.

Figure 6:
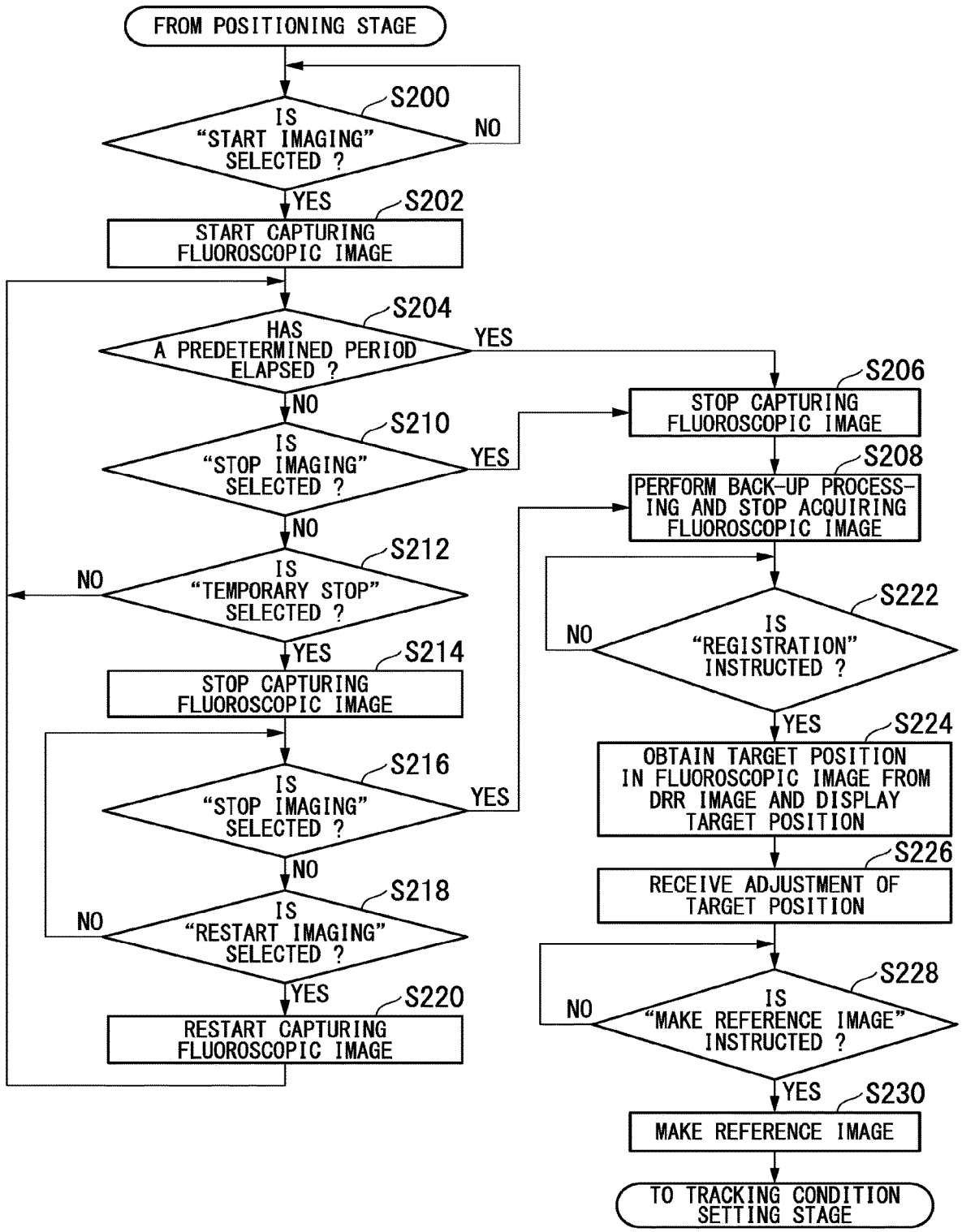
FIG. 6 is a flowchart illustrating an example of a flow of processing executed by the medical apparatus 100 in response to operations of the first button B1 and the second button B2 in a reference image making stage.

Hereinafter, various functions of the interface image IM will be described with reference to the flowchart regarding the reference image making stage, the tracking condition setting stage, and the therapy stage. FIG. 6 is a flowchart illustrating an example of a flow of processing executed by the medical apparatus 100 in the reference image making stage (Step S122) of the preparation stage (Step S120). After the positioning stage (Step S110), first, with reference to the information input from the input operation acquirer 122, the general controller 110 determines whether or not "start imaging" is selected by operating the first button B1 (Step S200). In the following description, in a case where it is detected that an operation has been performed with respect to the medical apparatus 100, the general controller 110 is regarded to perform determination with reference to information input from the input operation acquirer 122, and description for each case will be omitted.

In a case where the general controller 110 determines that "start imaging" has been selected by operating the first button B1, the general controller 110 instructs the output controller 150 to cause the therapeutic device 10 to capture the fluoroscopic image TI (Step S202). The acquirer 130 acquires the captured fluoroscopic image TI and stores the captured fluoroscopic image TI in the image storing memory 162. The output controller 150 may output an instruction for ending imaging to the therapeutic device 10 in a case where the first button B1 is operated again. In this manner, the output controller 150 outputs an instruction for an operation to the imager (the radiation sources 12-1 and 12-2, and the detectors 13-1 and 13-2) of the therapeutic device 10 in accordance with the details of the input operation acquired by the input operation acquirer 122. Accordingly, the medical apparatus 100 can manage an operation of the therapy system 1 including the therapeutic device 10 in an integrated manner, so that convenience is improved. Next, the general controller 110 determines whether or not a predetermined period designated in advance has elapsed from the start of imaging (Step S204). For example, a predetermined period is a period for a predetermined number of respiratory cycles. A respiratory cycle appears as a cyclical change in a series of fluoroscopic images TI. Therefore, the general controller 110 can determine whether or not a predetermined period has elapsed, based on the fluoroscopic image TI. That is, for example, the general controller 110 instructs the image processor 136 to determine the number of times of appearance of a cyclical change in the fluoroscopic images TI in real time from the start of imaging based on comparison and contrast of a series of the fluoroscopic images TI. For example, in a case where the predetermined period is a period for k times of respiratory cycles, the general controller 110 determines that a predetermined period has elapsed from the start of imaging, in a case where the image processor 136 determines that a k-th cyclical change from the start of imaging has appeared in the fluoroscopic image TI.

In a case where the general controller 110 determines that a predetermined period has elapsed from the start of imaging, the general controller 110 causes the output controller 150 to instruct the therapeutic device 10 to stop capturing the fluoroscopic image TI (Step S206). The general controller 110 transfers at least a part the fluoroscopic images TI stored in the image storing memory 162 to the back-up storage device 164 (Step S208; which will hereinafter be referred to as "back-up processing"). For example, such back-up processing is performed for the purpose of backing up the data of the fluoroscopic image TI, in preparation for a case in which therapeutic data cannot be read or is vanished due to malfunction of the device or the like. The general controller 110 performs the back-up processing described above and controls the acquirer 130 to be in a state of not receiving the fluoroscopic image TI even if the imager 30 sends the fluoroscopic image TI to the acquirer 130.

That is, the general controller 110 stops the acquirer 130 from acquiring the fluoroscopic image TI.

On the other hand, in a case where the general controller 110 determines that a predetermined period has not elapsed from the start of imaging, the general controller 110 determines whether or not "stop imaging" is selected by operating the first button B1 (Step S210). In a case where the general controller 110 determines that "stop imaging" has been selected by operating the first button B1, the general controller 110 causes the output controller 150 to instruct the therapeutic device 10 to stop capturing the fluoroscopic image TI (Step S206). The general controller 110 performs back-up processing and stops the acquirer 130 from acquiring the fluoroscopic image TI (Step S208).

In a case where the general controller 110 determines that "stop imaging" has not been selected by operating the first button B1, the general controller 110 determines whether or not "temporary stop" of imaging is selected by operating the second button B2 (Step S212). In a case where the general controller 110 determines that "temporary stop" of imaging has been selected by operating the second button B2, the general controller 110 causes the output controller 150 to instruct the therapeutic device 10 to stop capturing the fluoroscopic image TI (Step S214). However, the general controller 110 does not perform the back-up processing described above.

In this case, the general controller 110 does not control the acquirer 130 to be in a state of not receiving the fluoroscopic image TI from the imager 30. That is, the general controller 110 does not stop the acquirer 130 from acquiring the fluoroscopic image TI. Therefore, the acquirer 130 remains in a state of receiving the fluoroscopic image TI in a case where the imager 30 sends the fluoroscopic image TI to the acquirer 130. In a case where the general controller 110 determines that "temporary stop" of imaging has not been selected by operating the second button B2, the general controller 110 returns to Step S204 and determines whether or not a predetermined period designated in advance has elapsed from the start of imaging.

After imaging is temporarily stopped, the general controller 110 determines whether or not "stop imaging" is selected by operating the first button B1 (Step S216). In a case where the general controller 110 determines that "stop imaging" has been selected by operating the first button B1, the general controller 110 performs back-up processing and stops the acquirer 130 from acquiring the fluoroscopic image TI (Step S208).

In a case where the general controller 110 determines that "stop imaging" has not been selected by operating the first button B1, the general controller 110 determines whether or not "restart imaging" is selected by operating the second button B2 (Step S218). In a case where the general controller 110 determines that B2 "restart imaging" has been selected by operating the second button, the general controller 110 causes the output controller 150 to instruct the therapeutic device 10 to restart capturing the fluoroscopic image TI (Step S220). Thereafter, the general controller 110 returns to Step S204 and determines whether or not a predetermined period designated in advance has elapsed from the start of imaging.

In a case where the general controller 110 determines that "restart imaging" has not been selected by operating the second button B2, the general controller 110 returns to Step S216 and determines whether or not "stop imaging" is selected by operating the first button B1.

In a case where the general controller 110 determines, in Step S204, that a predetermined period has elapsed or determines, in Step S210 or Step S216, that "stop imaging" has been selected by operating the first button B1, the general controller 110 may cause the output controller 150, in Step S208, to instruct the therapeutic device 10 to end the state in which irradiation of the radiations r-1 and r-2 can be performed. The state in which irradiation of radiations can be performed denotes a state in which irradiation of radiations can be immediately performed in a case where an instruction for performing irradiation of radiations is received. In a case where the output controller 150 instructs the therapeutic device 10 to end the state in which irradiation of the radiations r-1 and r-2 can be performed, the therapeutic device 10 stops synchronization control of the radiation sources 12-1 and 12-2, for example. In this case, initialization or the like of synchronization signals of the radiation sources 12-1 and 12-2 may be required in order to restart irradiation of the radiations r-1 and r-2. In a case where the state in which irradiation of the radiations r-1 and r-2 can be performed ends as described above, the therapeutic device 10 is in a state of not receiving an instruction for performing irradiation of the radiations r-1 and r-2 (that is, an instruction for capturing the fluoroscopic image TI). Only in a case where the general controller 110 determines, in Step S204, that a predetermined period has elapsed, the general controller 110 may cause the output controller 150 to instruct the therapeutic device 10 to end the state in which irradiation of radiations can be performed.

On the contrary, only in a case where the general controller 110 determines, in Step S210 or Step S216, that "stop imaging" has been selected by operating the first button B1, the general controller 110 may cause the output controller 150 to instruct the therapeutic device 10 to end the state in which irradiation of radiations can be performed.

On the other hand, in a case where the general controller 110 determines, in Step S212, that "temporary stop" has been selected by operating the second button B2, the general controller 110 may cause the output controller 150, in Step S214, to instruct the therapeutic device 10 to maintain the state in which irradiation of the radiations r-1 and r-2 can be performed and to stop irradiation of the radiations r-1 and r-2. In this case, for example, the therapeutic device 10 retains a state in which communication with respect to the radiation sources 12-1 and 12-2 is established, by maintaining synchronization control of the radiation sources 12-1 and 12-2. Accordingly, the radiation sources 12-1 and 12-2 are maintained in a state in which irradiation of the radiations r-1 and r-2 can be immediately performed in response to an instruction for performing irradiation of radiations, without performing initialization or the like of synchronization signals.

Next, the general controller 110 determines whether or not registration is instructed by operating the fourth button B4 (Step S222).

In a case where registration is instructed by operating the fourth button B4, the general controller 110 instructs the image processor 136 to obtain a target position in the fluoroscopic image TI from the target position PT in a DRR image, and instructs the display controller 124 to cause the input/display 120 to display the obtained target position PT in a manner of being superimposed on the fluoroscopic image TI (Step S224). As described above, the image processor 136 performs processing of matching characteristic portions in images between the DRR image of which the target position PT is already known and the fluoroscopic image TI, based on the DRR image made from a CT image captured in the planning stage, or the fluoroscopic image TI captured after the planning stage, thereby deriving out the target position PT in the fluoroscopic image TI. The relationship between the fluoroscopic image TI and the target position PT is provided for the reference image maker 132. An image in which the target position PT is superimposed on the fluoroscopic image TI is displayed in the regions A1-1 and A1-2 of the interface image IM, for example. In this state, the general controller 110 receives an adjustment of the target position PT (Step S226). For example, the target position PT is adjusted by performing a drag/drop operation with respect to the regions A1-1 and A1-2. In a case where the target position PT is adjusted, the general controller 110 provides the adjusted relationship between the fluoroscopic image TI and the target position PT for the reference image maker 132.

Next, the general controller 110 determines whether or not making a reference image is instructed by operating the fifth button B5 (Step S228). In a case where the fifth button B5 is operated, the general controller 110 instructs the reference image maker 132 to select the fluoroscopic image TI to be used as a reference image and to perform processing such as resizing, thereby making a reference image (Step S230). The reference image maker 132 makes a reference image (template) with which the target position PT is associated and causes the storage 160 to store the reference image.

Figure 7:
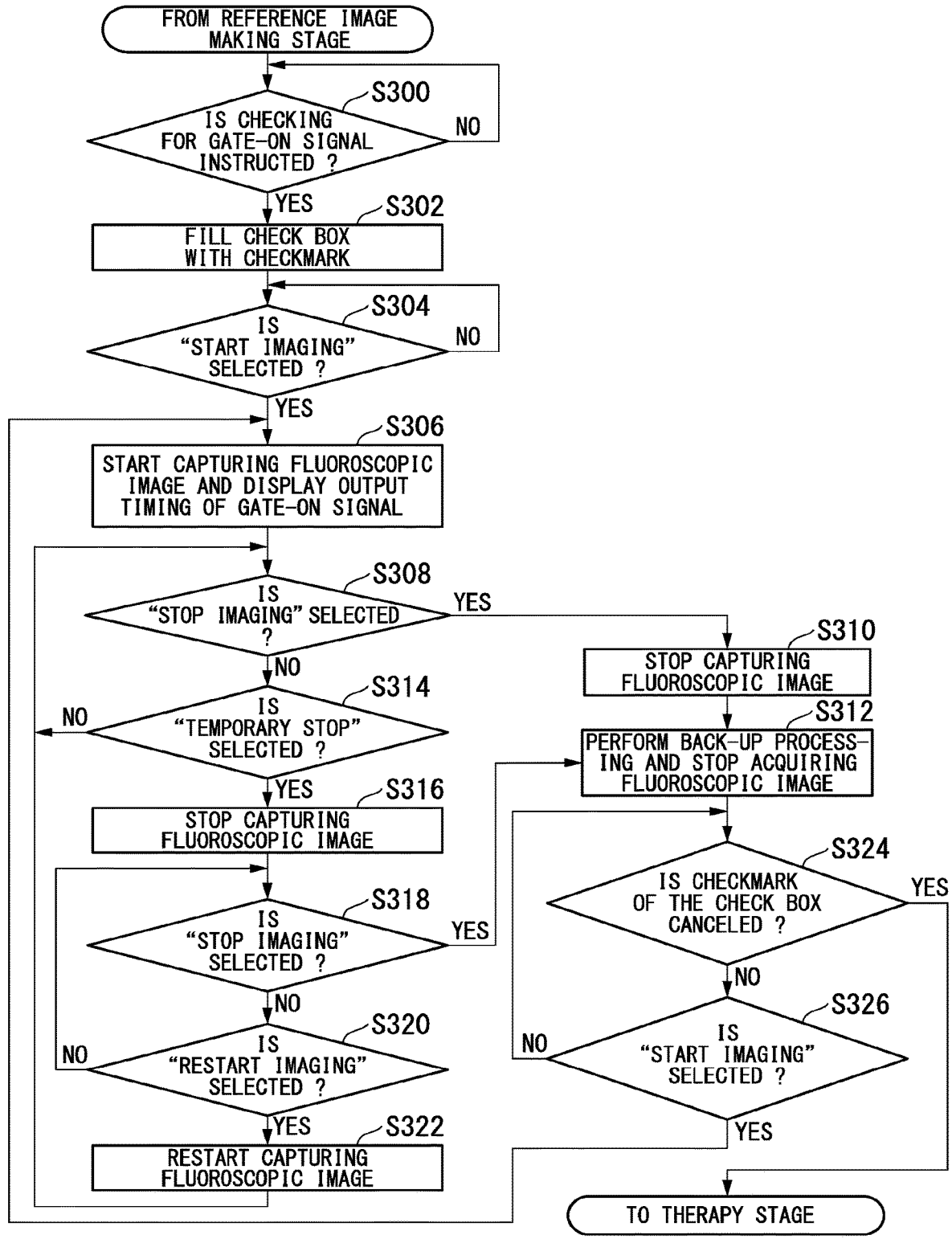
FIG. 7 is a flowchart illustrating an example of a flow of processing executed by the medical apparatus 100 in response to operations of the first button B1 and the second button B2 in a tracking condition setting stage.

FIG. 7 is a flowchart illustrating an example of a flow of processing executed by the medical apparatus 100 in the tracking condition setting stage (Step S124) of the preparation stage (Step S120). First, the general controller 110 determines whether or not checking for a gate-on signal is instructed by operating the sixth button B6 (Step S300). In a case where checking for a gate-on signal is instructed, the general controller 110 instructs the display controller 124 to change the check box CB into a state filled with a checkmark and causes the input/display 120 to display the output timing of a gate-on signal (Step S302). In the state in which the check box CB is filled with a checkmark, the output timing of a gate-on signal is calculated and displayed, but a gate-on signal is not actually output to the therapeutic device 10. The check box CB may be manually changed into a state filled with a checkmark.

Next, the general controller 110 determines whether or not "start imaging" is selected by operating the first button B1 (Step S304). In a case where "start imaging" is selected by operating the first button B1, the general controller 110 instructs the output controller 150 to instruct the therapeutic device 10 to capture the fluoroscopic image TI and instructs the display controller 124 to cause the input/display 120 to display a checking image using the captured fluoroscopic image TI (Step S306). The acquirer 130 acquires the captured fluoroscopic image TI and stores the captured fluoroscopic image TI in the image storing memory 162. In the present embodiment, in the tracking condition setting stage, if a predetermined period elapses from the start of imaging as in the reference image making stage, control of automatically stopping imaging is not performed. However, such control may be performed in the tracking condition setting stage.

The checking image is displayed in the regions A1-1 and A1-2. The checking image is an image in which the target position PT or the gating window GW is superimposed on the fluoroscopic image TI which is reproduced as a moving image (refer to FIG. 3). The output controller 150 outputs a gate-on signal to the display controller 124, which displays the gate-on signal in the region A2 in a case where the target position PT is settled in the gating window GW. A physician or the like can check for whether or not the target position PT such as a lesion of the object P is recognized as a correct position, whether or not the timing the target position PT is settled in the gating window GW is appropriate, the output efficiency of a gate-on signal, and the like, by visually recognizing this checking image. The checking image is displayed until "stop imaging" is selected by operating the first button B1. Even after stop imaging is selected, the checking image can be traced back and checked for by operating the control area CA in which the slide bar, the frame advancing switch, and the like are set.

After capturing the fluoroscopic image TI is started, the general controller 110 performs processing similar to that from Step S208 to Step S220 in the reference image making stage. That is, the general controller 110 determines whether or not "stop imaging" is selected by operating the first button B1 (Step S308). In a case where the general controller 110 determines that "stop imaging" has been selected by operating the first button B1, the general controller 110 causes the output controller 150 to instruct the therapeutic device 10 to stop capturing the fluoroscopic image TI (Step S310). Accordingly, the general controller 110 instructs the display controller 124 to stop displaying the presence or absence of an output of a checking image and a gate-on signal in the input/display 120. In this case, displaying at the point of time of stopping may remain displayed in the input/display 120. The general controller 110 performs back-up processing and stops the acquirer 130 from acquiring the fluoroscopic image TI (Step S312). On the other hand, in a case where the general controller 110 determines that "stop imaging" has not been selected by operating the first button B1 and determines that "temporary stop" of imaging has been selected by operating the second button B2 (Step S314), the general controller 110 cause the output controller 150 to instruct the therapeutic device 10 to stop capturing the fluoroscopic image TI, but does not perform back-up processing (Step S316). In this case, the general controller 110 does not stop the acquirer 130 from acquiring the fluoroscopic image TI, but similar to the case of "stop imaging", the general controller 110 instructs the display controller 124 to stop displaying the presence or absence of an output of a checking image and a gate-on signal in the input/display 120. In a case where the general controller 110 determines that "stop imaging" has been selected by operating the first button B1 during temporary stop of imaging (Step S318), the general controller 110 performs back-up processing and stops the acquirer 130 from acquiring the fluoroscopic image TI (Step S312). In a case where the general controller 110 determines that "restart imaging" has been selected by operating the second button B2 during temporary stop of imaging, the general controller 110 causes the output controller 150 to instruct the therapeutic device 10 to restart capturing the fluoroscopic image TI (Step S320). Accordingly, the general controller 110 instructs the display controller 124 to cause the input/display 120 to display a checking image and the presence or absence of an output of a gate-on signal again. Thereafter, the general controller 110 returns to Step S308 and determines whether or not "stop imaging" is selected by operating the first button B 1. Even in a case where the general controller 110 determines that "stop imaging" has not been selected by operating the first button B1 and determines that "temporary stop" of imaging has not been selected by operating the second button B2, the general controller 110 returns to Step S308 and determines whether or not "stop imaging" is selected by operating the first button B1.

Similar to the reference image making stage described above, in a case where the general controller 110 determines, in Step S308 or Step S318, that "stop imaging" has been selected by operating the first button B1, the general controller 110 may cause the output controller 150, in Step S312, to instruct the therapeutic device 10 to end the state in which irradiation of the radiations r-1 and r-2 can be performed. In a case where the general controller 110 determines, in Step S314, that "temporary stop" has been selected by operating the first button B1, the general controller 110 may cause the output controller 150, in Step S316, to instruct the therapeutic device 10 to maintain the state in which irradiation of the radiations r-1 and r-2 can be performed and to stop irradiation of the radiations r-1 and r-2.

After "stop imaging" is selected by operating the first button B1 and the fluoroscopic image TI is stopped being acquired, the general controller 110 determines whether or not the checkmark of the check box CB is canceled (Step S324). In a case where the checkmark of the check box CB is not canceled, the general controller 110 determines whether or not start imaging is selected by operating the first button B1 (Step S326). In a case where start imaging is selected, the processing returns to Step S306, and in a case where start imaging is not selected, the processing returns to Step S324. In a case where the checkmark of the check box CB is canceled, a therapy proceeds to the therapy stage (Step S130).

Figure 8:
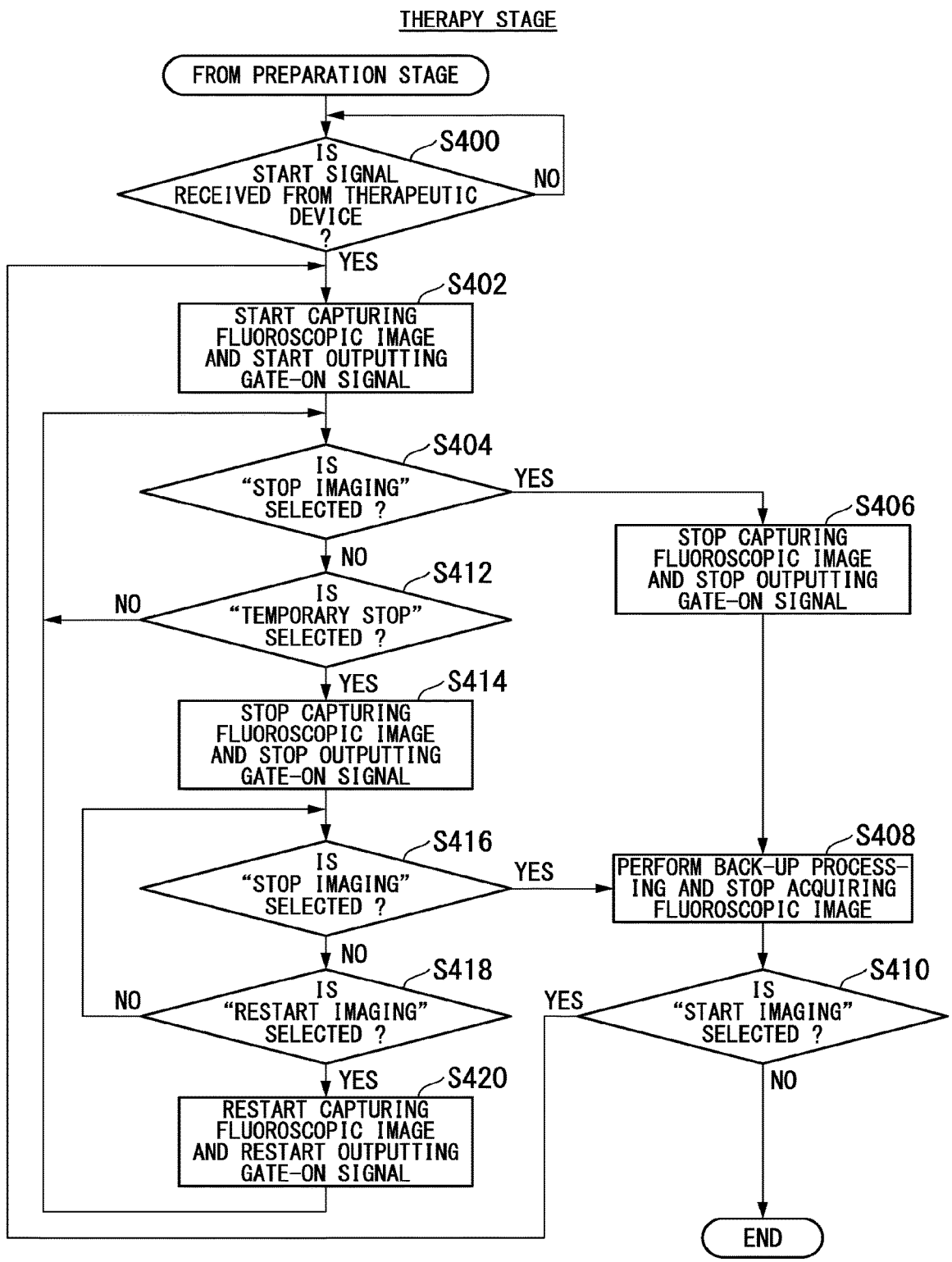
FIG. 8 is a flowchart illustrating an example of a flow of processing executed by the medical apparatus 100 in response to operations of the first button B1 and the second button B2 in a therapy stage.

FIG. 8 is a flowchart illustrating an example of a flow of processing executed by the medical apparatus 100 in the therapy stage (Step S130). First, the general controller 110 determines whether or not a start signal is received from the therapeutic device 10 (Step S400). This start signal is a signal output in a case where the therapeutic device 10 can start a therapy by operating a switch (not illustrated) of the therapeutic device 10. In a case where a start signal is received from the therapeutic device 10, the general controller 110 instructs the display controller 124, the target position identifier 140, and the output controller 150 to start a therapy (Step S402). In this manner, in the interface image IM, the output controller 150 outputs a gate-on signal to the therapeutic device 10 on condition that an input operation of causing a default state in Step S302 of the preparation stage (the tracking condition setting stage) to be a cancel state is acquired by the input operation acquirer 122. Accordingly, unintentional irradiation of the therapeutic beam B to the object P is suppressed, and reliability of a therapy can be enhanced. In a case where making a template is completed, without requiring an ending operation of the preparation stage, the input operation acquirer 122 receives an instruction to start the irradiation stage of the therapeutic beam B. Accordingly, it is possible to improve operability of the medical apparatus 100.

The target position identifier 140 performs matching of the fluoroscopic image TI and the template, thereby identifying the target position PT. The output controller 150 outputs a gate-on signal to the therapeutic device 10 in a case where the target position PT is settled in the gating window GW. The display controller 124 causes the input/display 120 to display a therapeutic image in which the target position PT or the gating window GW is superimposed on the fluoroscopic image TI. The therapeutic image is displayed in the regions A1-1 and A1-2. The acquirer 130 acquires the captured fluoroscopic image TI and stores the captured fluoroscopic image TI in the image storing memory 162. A therapy continues until "stop imaging" is selected by operating the first button B1. The medical apparatus 100 may end a therapy even in a case where a signal for completing irradiation is received from the therapeutic device 10 or in a case where a signal indicating that an operation of ending irradiation is conducted in the therapeutic device 10 is received from the therapeutic device 10. In this manner, the output controller 150 outputs an instruction for an operation to the imager (the radiation sources 12-1 and 12-2, and the detectors 13-1 and 13-2) of the therapeutic device 10, and a particular function (the target position identifier 140 or the like) of the medical apparatus 100 is activated in accordance with a unit-based input operation (an operation of the first button B1) acquired by the input operation acquirer 122. Accordingly, the medical apparatus 100 can manage an operation of the therapy system 1 including the therapeutic device 10 in an integrated manner, so that convenience is improved.

After capturing the fluoroscopic image TI and outputting a gate-on signal are started, the general controller 110 determines whether or not "stop imaging" is selected by operating the first button B1 (Step S404). In a case where the general controller 110 determines that "stop imaging" has been selected by operating the first button B1, the general controller 110 causes the output controller 150 to instruct the therapeutic device 10 to stop capturing the fluoroscopic image TI and stops outputting a gate-on signal (Step S406). The general controller 110 performs back-up processing and stops the acquirer 130 from acquiring the fluoroscopic image TI (Step S408). Thereafter, the general controller 110 determines whether or not "start imaging" is selected by operating the first button B1 (Step S410). In a case where the general controller 110 determines that "start imaging" has been selected by operating the first button B1, the general controller 110 returns to Step S402 and causes the output controller 150 to instruct the therapeutic device 10 to capture the fluoroscopic image TI and starts outputting a gate-on signal or permits starting an output of a gate-on signal. That is, even in a case where capturing the fluoroscopic image TI and outputting a gate-on signal are stopped, if "start imaging" is selected by operating the first button B1, capturing the fluoroscopic image TI and outputting a gate-on signal are started again, and a therapy is restarted.

On the other hand, in a case where the general controller 110 determines, in Step S404, that "stop imaging" has not been selected by operating the first button B1 and determines, in Step S412, that "temporary stop" of imaging has been selected by operating the second button B2, the general controller 110 causes the output controller 150 to instruct the therapeutic device 10 to stop capturing the fluoroscopic image TI and stops outputting a gate-on signal, but does not perform back-up processing (Step S414). In this case, the general controller 110 does not stop the acquirer 130 from acquiring the fluoroscopic image TI. In a case where the general controller 110 determines that "stop imaging" has been selected by operating the first button B1 during temporary stop of imaging, the general controller 110 performs back-up processing and stops the acquirer 130 from acquiring the fluoroscopic image TI (Step S408). In a case where the general controller 110 determines that "restart imaging" has been selected by operating the second button B2 during temporary stop of imaging, the general controller 110 causes the output controller 150 to instruct the therapeutic device 10 to capture the fluoroscopic image TI and to restart outputting a gate-on signal (Step S420). Thereafter, the general controller 110 returns to Step S404 and determines whether or not "stop imaging" is selected by operating the first button B1.

In a case where the general controller 110 determines, in Step S404 or Step S416, that "stop imaging" has been selected by operating the first button B1, the general controller 110 may cause the output controller 150, in Step S408, to instruct the therapeutic device 10 to end a state in which irradiation of the therapeutic beam B can be performed. The state in which irradiation of a therapeutic beam can be performed denotes a state in which irradiation of a therapeutic beam can be immediately performed in a case where a gate-on signal is received. In a case where the therapeutic beam B is a heavy particle beam or the like, if the output controller 150 instructs the therapeutic device 10 to end the state in which irradiation of the therapeutic beam B can be performed, the therapeutic device 10 instructs an accelerator generating the therapeutic beam B and stops supplying the therapeutic beam B to the therapeutic device 10, for example. In this case, the accelerator can be capable of supplying the therapeutic beam B to another therapeutic device 10.

At least a part of the functions of the accelerator for generating the therapeutic beam B may be stopped. In a case where the state in which irradiation of the therapeutic beam B can be performed ends as described above, the therapeutic device 10 is in a state of not receiving a gate-on signal.

On the other hand, in a case where the general controller 110 determines, in Step S412, that "temporary stop" has been selected by operating the first button B1, the general controller 110 may cause the output controller 150, in Step S414, to instruct the therapeutic device 10 to maintain the state in which irradiation of the therapeutic beam B can be performed.

In a case where the therapeutic beam B is a heavy particle beam or the like, if the output controller 150 instructs the therapeutic device 10 to maintain the state in which irradiation of the therapeutic beam B can be performed, the therapeutic device 10 instructs the accelerator generating the therapeutic beam B and to maintain a state in which supplying the therapeutic beam B to the therapeutic device 10 can be immediately restarted, for example. In this case, the supply route of the therapeutic beam B from the accelerator cannot be changed. The timing the therapeutic device 10 is in the state in which irradiation of the therapeutic beam B can be performed may be any time before the medical apparatus 100 receives a start signal from the therapeutic device 10.

In addition to the foregoing control regarding the therapeutic beam B, similar to the reference image making stage and the tracking condition setting stage described above, in a case where the general controller 110 determines, in Step S404 or Step S412, that "stop imaging" has been selected by operating the first button B1, the general controller 110 may cause the output controller 150, in Step S408, to instruct the therapeutic device 10 to end the state in which irradiation of the radiations r-1 and r-2 can be performed. In a case where the general controller 110 determines, in Step S412, that "temporary stop" has been selected by operating the first button B1, the general controller 110 may cause the output controller 150, in Step S414, to instruct the therapeutic device 10 to maintain the state in which irradiation of the radiations r-1 and r-2 can be performed and to stop irradiation of the radiations r-1 and r-2.

The display controller 124 may change the color of the gating window in a case where a gate-on signal is output (in the tracking condition setting stage, in a case where the conditions for outputting a gate-on signal are fulfilled) in the checking image and the therapeutic image. For example, regarding both the fluoroscopic images TI-1 and TI-2, the border line of the gating window GW may be displayed in a first color in a case where the target position PT is not settled in the gating window GW, may be displayed in a second color in a case where the target position PT is settled in the gating window GW in only one of both the fluoroscopic images TI-1 and TI-2, and may be displayed in a third color in a case where the target position PT is settled in the gating window GW (that is, in a case where the conditions for outputting a gate-on signal are fulfilled) in both the fluoroscopic images T1-1 and TI-2. An error icon may be displayed in a case where the target position PT is not settled in the gating window GW in both the fluoroscopic images TI-1 and TI-2.

In a case where the conditions for outputting a gate-on signal are fulfilled, the display controller 124 may change the hue or the brightness of any of an inner region and an outer region of the gating window GW. Moreover, the medical apparatus 100 may include a notifier that issues notification by a sound or a vibration in a case where the conditions for outputting a gate-on signal are fulfilled.

The general controller 110 can instruct the display controller 124 to cause the icon window IW of the input/display 120 to display an icon (for example, a mark of a light bulb) indicating that a gate-on signal is being output, while the gate-on signal is being output. Even in the tracking condition setting stage, the general controller 110 may instruct the display controller 124 to cause the icon window IW to display the icon while the conditions for outputting a gate-on signal are fulfilled.

As described above, the fluoroscopic image TI is captured even in a stage in which irradiation of the therapeutic beam B is not performed (for example, the preparation stage), or even in a stage in which irradiation of the therapeutic beam B is performed (for example, the therapy stage). However, the frame rate of capturing the fluoroscopic image TI in the preparation stage may be different from the frame rate of capturing the fluoroscopic image TI in the therapy stage. For example, the frame rate of capturing the fluoroscopic image TI in the preparation stage may be set to be lower than the frame rate of capturing the fluoroscopic image TI in the therapy stage. A frame rate is a frequency of capturing the fluoroscopic image TI. In a case where the frame rate increases, the time interval between two consecutively captured images becomes shorter. Therefore, movement of a portion inside the body to be image-captured can be minutely checked for.

Effect

According to such a configuration, efficiency of a therapy can be improved. That is, in the present embodiment, the medical apparatus 100 includes the acquirer 130 that acquires the fluoroscopic image TI of the object P from the imager 30 which performs imaging by irradiating the object P with an electromagnetic wave to generate the fluoroscopic image TI, the target position identifier 140 that identifies the target position PT of the object P in the fluoroscopic image TI, and the general controller 110 that outputs a gate-on signal to the therapeutic device 10 which irradiates the object P with the therapeutic beam B in a case where the target position PT identified by the target position identifier 140 is settled within the gating window GW. The general controller 110 causes the imager 30 to stop irradiation of an electromagnetic wave and stops the acquirer 130 from acquiring the fluoroscopic image TI, in a case where the second form of the first button B1 is operated. The general controller 110 causes the imager 30 to stop irradiation of an electromagnetic wave and maintains a state in which the acquirer 130 can acquire the fluoroscopic image TI, in a case where the third form of the second button B2 is operated. Therefore, a physician or the like can use "stop imaging" or "temporary stop" of imaging to serve its purposes and can select whether or not to stop acquiring the fluoroscopic image TI. In a case where a physician or the like intends to temporarily halt imaging or a therapy (for example, in a case where sneezing of a physician or the like or temporary abnormality of the condition of a patient has occurred), imaging is temporarily stopped by operating the second button B2, so that the time taken to restart imaging can be shortened.

In contrast, in a medical apparatus which does not include the second button B2, in a case where imaging or a therapy is stopped, a physician or the like stops imaging by operating the first button. Therefore, even in a case where a physician or the like intends to temporarily halt imaging or a therapy as described above, the acquirer stops acquiring a fluoroscopic image. In this case, there is a need to start acquiring a fluoroscopic image again in order to restart imaging or a therapy. However, there are cases in which it takes time to start acquiring a fluoroscopic image, so that the efficiency of a therapy may deteriorate, compared to the present embodiment.

In the present embodiment, the general controller 110 executes processing of transferring information of the fluoroscopic image TI, which has been acquired by the acquirer 130 and has been stored in the image storing memory 162, to the back-up storage device 164 in a case where the second form of the first button B1 is operated. According to such a configuration, in a case where capturing the fluoroscopic image TI is stopped, a physician or the like can select whether or not to perform processing of transferring information of the fluoroscopic image TI to the back-up storage device 164, by using the first button B1 or the second button B2 to serve its purpose. Therefore, for example, in a case where a physician or the like intends to temporarily halt imaging, back-up processing described above is performed every time and the acquirer 130 can avoid a state of not receiving the fluoroscopic image TI. In a case where back-up processing is performed, there may be cases in which it takes time to restart imaging due to stopping of the function of the acquirer 130 taking the fluoroscopic image TI, or there may be cases in which the acquirer 130 fails to acquire the fluoroscopic image TI in the middle of being transmitted to the acquirer 130. However, according to the foregoing configuration, back-up processing is not performed in a case where imaging is temporarily stopped. Therefore, efficiency of a therapy can be improved.

In the present embodiment, the general controller 110 stops outputting a gate-on signal in a case where the second form of the first button B1 or the third form of the second button B2 is operated in a state in which the object P is irradiated with the therapeutic beam B. According to such a configuration, in a case where "stop imaging" or "temporary stop" of imaging is selected by operating the second form of the first button B1 or the third form of the second button B2, outputting a gate-on signal can also be stopped. Imaging and outputting a gate-on signal are interlocked with each other in this manner. Therefore, compared to a case in which a physician or the like has to separately operate buttons to stop imaging and to stop outputting a gate-on signal, effort of the physician or the like can be omitted, and the exposure dose of a patient can be reduced.

In the present embodiment, in a case where the first form of the first button B1 is operated, the general controller 110 instructs the imager 30 to start imaging during the preparation stage and starts outputting a gate-on signal during the therapy stage. According to such a configuration, the presence or absence of an output of a gate-on signal is automatically controlled depending on the mode. Therefore, even in a case where an instruction irradiation of the therapeutic beam B is erroneously input in the preparation stage, the instruction for irradiation can be blocked. Accordingly, a possibility that irradiation of the therapeutic beam B is erroneously performed in the preparation stage can be reduced. A physician or the like can issue an instruction for start imaging in both the preparation stage and the therapy stage by operating the common first button B1. Accordingly, convenience of the medical apparatus 100 can be improved.

In the present embodiment, the general controller 110 instructs the imager 30 to perform imaging for a predetermined period in a case where the first form of the first button B1 is operated in the reference image making stage. According to such a configuration, in a case where imaging for a predetermined period is completed, imaging is automatically stopped. Therefore, there is no need for a physician or the like to operate the first button B1 in order to stop acquiring the fluoroscopic image TI in the reference image making stage. Although, there are cases in which the period of imaging is excessively shortened by mistake in a case where a physician or the like manually stops imaging, such a situation can be prevented. Moreover, since a predetermined period which is necessary and sufficient to make a reference image is set in advance, a reference image can be stably made every time.

Therefore, convenience of the medical apparatus 100 can be improved.

In the present embodiment, a predetermined period is a period for a respiratory cycle designated in advance. According to such a configuration, a reference image is automatically made from the fluoroscopic images TI for one or more respiratory cycles. Therefore, the number of fluoroscopic images TI which are not used for making a reference image can he reduced. Accordingly, the exposure dose of a patient can he reduced.

In the present embodiment, the output controller 150 causes therapeutic device 10 to end a state in which irradiation of an electromagnetic wave can be performed, in a case where the second form of the first button B1 is operated, and the output controller 150 causes therapeutic device 10 to maintain the state in which irradiation of an electromagnetic wave can be performed, in a case where the third form of the second button B2 is operated. According to such a configuration, in a case where a physician or the like desires to temporarily stop a therapy, the therapeutic device 10 can be immediately maintained in the state in which irradiation of an electromagnetic wave can be performed, by operating the third form of the second button B2. If the state in which irradiation of an electromagnetic wave can be performed ends once, it may take time and effort to return to the state in which irradiation of an electromagnetic wave can be performed. However, since a physician or the like can select "stop imaging" or "temporary stop" as described above, efficiency of a therapy can be improved.

In the present embodiment, in a state in which the therapeutic device 10 can perform irradiation of the therapeutic beam B, the output controller 150 causes the therapeutic device 10 to end the state in which irradiation of the therapeutic beam B can be performed, in a case where the second form of the first button B1 is operated, and the output controller 150 causes the therapeutic device 10 to maintain the state in which irradiation of the therapeutic beam B can be performed, in a case where the third form of the second button B2 is operated. According to such a configuration, similar to that described above, in a case where a physician or the like desires to temporarily stop a therapy, the therapeutic device 10 can he immediately maintained in the state in which irradiation of the therapeutic beam B can be performed, by operating the third form of the second button B2. Accordingly, efficiency of a therapy can be improved.

In the present embodiment, the medical apparatus 100 further includes the display controller 124 that causes the input/display 120 to display a predetermined icon while a gate-on signal is being output. According to such a configuration, a physician or the like can easily and visually recognize the presence or absence of an output of a gate-on signal. Accordingly, a physician or the like can easily understand the interface image IM displayed by the input/display 120. Therefore, convenience of the medical apparatus 100 can be improved.

In the present embodiment, the frame rate of capturing the fluoroscopic image TI in the preparation stage is set to be lower than the frame rate of capturing the fluoroscopic image TI in the therapy stage. According to such a configuration, the frame rate in the preparation stage is low. Therefore, compared to a case in which the preparation stage and the therapy stage have a common frame rate, the exposure dose of a patient in the preparation stage can be reduced. The fluoroscopic images TI for more respiratory cycles can be captured by lengthening the period of imaging, instead of lowering the frame rate in the preparation stage. Therefore, a physician or the like can observe the fluoroscopic images TI for respiratory cycles of various patterns (for example, various depths of respirations). Accordingly, a physician or the like can make an optimal reference image without increasing the number of captured images. Therefore, efficiency of making a reference image can be improved.

Modification Example

In each of the steps in the flowchart described in the foregoing embodiment as an example, unless it is against its nature, the execution order may be changed, a plurality of steps may be performed at the same time, or the steps may be performed in a different order every time the steps are performed.

In the foregoing embodiment, the therapeutic device 10 and the medical apparatus 100 are described as separate devices. However, the therapeutic device 10 and the medical apparatus 100 may be an integrated device. In a case where the therapeutic device 10 and the medical apparatus 100 are separate devices, the therapeutic device-side controller 20 may be a function built inside the medical apparatus 100.

An image used for the therapeutic plan is not limited to a 4D CT image, and other moving images of three-dimensional volume data may be used. For example, it may be a moving image of magnetic resonance imaging (MRI).

In the foregoing embodiment, the reference image making stage, the tracking condition setting stage, and the therapy stage are described. However, the foregoing operation can also be applied to other stages. For example, in the positioning stage, the flow of processing executed by the medical apparatus 100 in response to operations of the first button B1 and the second button B2 may be a flow similar to the flow of the processing described in regard to the tracking condition setting stage. In the foregoing embodiment, both "start imaging" and "stop imaging" can be instructed by operating the first button B1. However, a button corresponding to "start imaging" and a button corresponding to "stop imaging" may be provided one each. Similarly, in the foregoing embodiment, both "temporary stop" and "restart imaging" can be instructed by operating the second button B2. However, a button corresponding to "temporary stop" and a button corresponding to "restart imaging" may be provided one each. In this case, a button corresponding to "stop imaging" is an example of "the first switch", a button corresponding to "temporary stop" is an example of "the second switch", and a button corresponding to "start imaging" is an example of "the third switch". In the foregoing embodiment, in the reference image making stage, the image processor 136 performs comparison and contrast of the fluoroscopic images TI to determine whether a predetermined period has elapsed from the start of imaging. However, the general controller 110 may determine whether or not a predetermined period designated in advance has elapsed from the start of imaging by utilizing information from the sensor 15 which recognizes the external respiratory phase of the object P. In the foregoing embodiment, in the reference image making stage, capturing the fluoroscopic image TI is automatically stopped after a predetermined period has elapsed from the start of capturing the fluoroscopic image TI. However, a physician or the like may manually stop imaging without executing such automatic stopping. In the foregoing embodiment, in the reference image making stage, the acquired fluoroscopic image TI can be used as a reference image not only in a case where acquiring the fluoroscopic image TI is stopped with the lapse of a predetermined period but also in a case where acquiring the fluoroscopic image TI is stopped by a physician or the like operating the first button B1 to select stop imaging, before a predetermined period elapses. However, the fluoroscopic image TI in the latter case does not have to be used as a reference image.

In the foregoing embodiment, the general controller 110 causes the acquirer 130 to stop acquiring the fluoroscopic image TI in a case where "stop imaging" is selected, and the general controller 110 does not cause the acquirer 130 to stop acquiring the fluoroscopic image TI in a case where "temporary stop" is selected. In addition, in the foregoing description, it has been described that the state in which irradiation of an electromagnetic wave or the therapeutic beam B can be performed may be further controlled in accordance with selection of "stop imaging" or "temporary stop". However, in another embodiment, the general controller 110 may cause the therapeutic device 10 to end a state in which irradiation of one or both an electromagnetic wave and the therapeutic beam B can be performed, in a case where "stop imaging" is selected, and the general controller 110 may cause the therapeutic device 10 to maintain the state in which irradiation of one or both an electromagnetic wave and the therapeutic beam B can be performed, in a case where "temporary stop" is selected. On the other hand, stop acquiring the fluoroscopic image TI does not have to be controlled in accordance with selection of "stop imaging" or "temporary stop". That is, in another embodiment, the general controller 110 may cause the acquirer 130 to stop acquiring the fluoroscopic image TI or does not have cause the acquirer 130 to stop acquiring the fluoroscopic image TT.

The control method for a medical apparatus described in the foregoing embodiment is a control method for a medical apparatus in which a computer acquires a fluoroscopic image of an object from an imaging device which performs imaging by irradiating the object with an electromagnetic wave to generate the fluoroscopic image, identifies a target position of the object in the fluoroscopic image, outputs a gate-on signal to a therapeutic device which irradiates the object with a therapeutic beam in a case where the identified target position is settled within a gating window, causes the imaging device to stop irradiation of the electromagnetic wave and to stop acquiring the fluoroscopic image in a case where a first switch is operated, and causes the imaging device to stop irradiation of the electromagnetic wave and to maintain a state of being capable of acquiring the fluoroscopic image in a case where a second switch is operated.

The medical program described in the foregoing embodiment is a medical program causing a computer to acquire a fluoroscopic image of an object from an imaging device which performs imaging by irradiating the object with an electromagnetic wave to generate the fluoroscopic image, to identify a target position of the object in the fluoroscopic image, to output a gate-on signal to a therapeutic device which irradiates the object with a therapeutic beam in a case where the identified target position is settled within a gating window, to cause the imaging device to stop irradiation of the electromagnetic wave and to stop acquiring a fluoroscopic image in a case where a first switch is operated, and to cause the imaging device to stop irradiation of the electromagnetic wave and to maintain a state of being capable of acquiring the fluoroscopic image in a case where a second switch is operated.

The embodiment described above can be expressed as follows.

A medical apparatus is configured to include a hardware processor, and a storage device.

The hardware processor executes the program stored in the storage device to acquire a fluoroscopic image of an object from an imaging device which performs imaging by irradiating the object with an electromagnetic wave to generate the fluoroscopic image, to identify a target position of the object in the fluoroscopic image, to output an irradiation permission signal to a therapeutic device which irradiates the object with a therapeutic beam in a case where the identified target position is settled within an irradiation permission range, to cause the imaging device to stop irradiation of the electromagnetic wave and to stop acquiring the fluoroscopic image in a case where a first switch is operated, and to cause the imaging device to stop irradiation of the electromagnetic wave and to maintain a state of being capable of acquiring the fluoroscopic image in a case where a second switch is operated.

According to at least one embodiment described above, the general controller causes the imager to stop irradiation of the electromagnetic wave and causes the acquirer to stop acquiring the fluoroscopic image in a case where the second form of the first button is operated, and causes the imager to stop irradiation of the electromagnetic wave and to maintain a state in which the acquirer can acquire the fluoroscopic image in a case where the third form of the second button is operated. Therefore, efficiency of a therapy can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical apparatus comprising:
an acquirer configured to acquire a fluoroscopic image of an object from an imager which performs imaging by irradiating the object with an electromagnetic wave to generate the fluoroscopic image;
an identifier configured to identify a target position of the object in the fluoroscopic image; and
a controller configured to output an irradiation permission signal to a therapeutic device which irradiates the object with a therapeutic beam in a case where the target position identified by the identifier is settled within an irradiation permission range,
wherein the controller is configured to cause the imager to stop performing irradiation of the electromagnetic wave and cause the acquirer to stop acquiring the fluoroscopic image, in a case where a first switch is operated, and the controller is configured to cause the imager to stop performing irradiation of the electromagnetic wave and maintain a state in which the acquirer is capable of acquiring the fluoroscopic image, in a case where a second switch is operated.

2. The medical apparatus according to claim 1,
wherein the controller is configured to execute processing of transferring information of the fluoroscopic image, which has been acquired by the acquirer and has been stored in a memory, to a storage device in a case where the first switch is operated.

3. The medical apparatus according to claim 1,
wherein the controller is configured to stop outputting the irradiation permission signal, in a case where the first switch or the second switch is operated in a state in which the object can be irradiated with the therapeutic beam.

4. The medical apparatus according to claim 1,
wherein the controller is configured to instruct the imager to start imaging in a case where a third switch is operated during a preparation stage and instruct the imager to start imaging and permit starting an output of the irradiation permission signal in a case where the third switch is operated during a therapy stage.

5. The medical apparatus according to claim 1,
wherein the controller is configured to instruct the imager to perform imaging by irradiating the object with the electromagnetic wave at a first interval in a case where a third switch is operated during a preparation stage and instruct the imager to perform imaging by irradiating the object with the electromagnetic wave at a second interval different from the first interval in a case where a third switch is operated during a therapy stage.

6. The medical apparatus according to claim 4,
wherein the controller is configured to instruct the imager to perform imaging for a predetermined period, in a case where the third switch is operated in a reference image making stage.

7. The medical apparatus according to claim 6,
wherein the predetermined period is a period for a respiratory cycle designated in advance.

8. The medical apparatus according to claim 1, further comprising:
a display controller configured to cause a display to display a predetermined icon while the irradiation permission signal is being output.

9. The medical apparatus according to claim 1, further comprising:
a display controller configured to cause the irradiation permission range to be displayed in a manner of being superimposed on the fluoroscopic image and change a color of the irradiation permission range in a case where the irradiation permission signal is output.

10. The medical apparatus according to claim 1, further comprising:
a display controller configured to cause the irradiation permission range to be displayed in a manner of being superimposed on the fluoroscopic image and change a hue or brightness of any of an inner region or an outer region of the irradiation permission range in a case where the irradiation permission signal is output.

11. The medical apparatus according to claim 1, further comprising:
a notifier configured to issue notification by a sound or a vibration in a case where the irradiation permission signal is output.

12. A medical apparatus comprising:
an acquirer configured to acquire a fluoroscopic image of an object from an imager which performs imaging by irradiating the object with an electromagnetic wave to generate the fluoroscopic image;
an identifier configured to identify a target position of the object in the fluoroscopic image; and
a controller configured to output an irradiation permission signal to a therapeutic device which irradiates the object with a therapeutic beam in a case where the target position identified by the identifier is settled within an irradiation permission range,
wherein the controller is configured to cause the therapeutic device to end a state of being capable of performing irradiation of the electromagnetic wave, in a case where a first switch is operated, and the controller is configured to cause the therapeutic device to maintain the state of being capable of performing irradiation of the electromagnetic wave, in a case where a second switch is operated.

13. A medical apparatus comprising:
an acquirer configured to acquire a fluoroscopic image of an object from an imager which performs imaging by irradiating the object with an electromagnetic wave to generate the fluoroscopic image;
an identifier configured to identify a target position of the object in the fluoroscopic image; and
a controller configured to output an irradiation permission signal to a therapeutic device which irradiates the object with a therapeutic beam in a case where the target position identified by the identifier is settled within an irradiation permission range,
wherein the controller is configured to cause the therapeutic device to end a state of being capable of performing irradiation of the therapeutic beam, in a case where a first switch is operated, and the controller is configured to cause the therapeutic device to maintain the state of being capable of performing irradiation of the therapeutic beam, in a case where a second switch is operated, in a state in which the therapeutic device is capable of performing irradiation of the therapeutic beam.

14. A method executed by a medical apparatus, comprising:
acquiring a fluoroscopic image of an object from an imaging device which performs imaging by irradiating the object with an electromagnetic wave to generate the fluoroscopic image;
identifying a target position of the object in the fluoroscopic image;
outputting an irradiation permission signal to a therapeutic device which irradiates the object with a therapeutic beam in a case where the identified target position is settled within an irradiation permission range, and
causing the imaging device to stop performing irradiation of the electromagnetic wave and stop acquiring the fluoroscopic image, in a case where a first switch is operated, and causing the imaging device to stop performing irradiation of the electromagnetic wave and maintaining a state of being capable of acquiring the fluoroscopic image, in a case where a second switch is operated.

* * * * *